United States Patent
Harren et al.

[11] Patent Number: 6,007,562
[45] Date of Patent: Dec. 28, 1999

[54] PUNCTURE CLOSURE

[75] Inventors: Ernst-Diethelm Harren, Würselen; Christian Bangert, Aachen, both of Germany

[73] Assignee: CAP Incorporated, Panama, Panama

[21] Appl. No.: 08/796,162

[22] Filed: Feb. 14, 1997

Related U.S. Application Data

[63] Continuation of application No. PCT/DE95/01108, Aug. 17, 1995.

[30] Foreign Application Priority Data

Aug. 18, 1994 [DE] Germany ............... 44 29 230

[51] Int. Cl.⁶ ................................................ A61B 17/00
[52] U.S. Cl. ................................................ 606/213
[58] Field of Search ...................... 606/213, 201–204, 606/214; 602/46–58

[56] References Cited

U.S. PATENT DOCUMENTS

| | | | |
|---|---|---|---|
| 1,441,656 | 1/1923 | Bosse | 602/53 |
| 3,171,410 | 3/1965 | Towle, Jr. et al. | 606/215 |
| 3,490,448 | 1/1970 | Grubb | 602/46 |
| 3,739,773 | 6/1973 | Schmitt et al. | 602/46 |
| 3,954,109 | 5/1976 | Patel . | |
| 4,224,945 | 9/1980 | Cohen | 606/215 |
| 4,460,370 | 7/1984 | Allison et al. | 606/215 |
| 5,180,360 | 1/1993 | Rhame, Jr. | 602/53 X |
| 5,209,718 | 5/1993 | McDaniel | 602/53 |
| 5,234,459 | 8/1993 | Lee . | |
| 5,259,835 | 11/1993 | Clark et al. | 602/48 |
| 5,690,610 | 11/1997 | Ito et al. | 602/53 |
| 5,728,071 | 3/1998 | Watson et al. | 602/46 |

FOREIGN PATENT DOCUMENTS

| | | |
|---|---|---|
| 0514026 | 11/1992 | European Pat. Off. . |
| 0554602 | 8/1993 | European Pat. Off. . |

*Primary Examiner*—Michael Buiz
*Assistant Examiner*—Vikki Trinh
*Attorney, Agent, or Firm*—Thomas R. Vigil

[57] ABSTRACT

The puncture closure for closing a blood vessel with a puncture, in particular an artery, a vein short circuited with an artery, a shunt or a prosthesis, etc. has a pressure chamber in which an overpressure may be created, provided with an opening for receiving a pressure medium and fastenable to the body in the area of the puncture. The part of the pressure chamber that faces the body is extensible. In order to create a puncture closure that reliably closes the puncture of a blood vessel without too much blood loss, without forming significant hematomas nor completely collapsing the blood vessel, the opening for receiving the pressure medium is located above a piercing channel of the puncture hole and the blood that flows out of the blood vessel is used as a pressure medium.

18 Claims, 3 Drawing Sheets

PUNCTURE CLOSURE

CROSS-REFERENCE TO RELATED APPLICATIONS

This is a continuation of International Application PCT/DE 95/01108 with an International Filing Date of Aug. 17, 1995.

BACKGROUND OF THE INVENTION

1. Field of the invention

The invention relates to a puncture closure for closing a puncture of a blood vessel, particularly of an artery, a vein short circuited with an artery, a shunt or a prosthesis and the like being under arterial pressure, this puncture closure has a pressure chamber, which can be loaded with excess pressure, as well as an opening for receiving the pressure medium and can be fastened onto the body in the vicinity of the puncture, whereas the body facing part of the pressure chamber is extensible.

Blood vessels within the scope of the present invention are all arterial vessels, i.e. all vessels leading away from the heart or vessels being under arterial pressure (133,322–266, 644 mbar). Thus veins short circuited with an artery, and prosthesis connected to arteries (interpositions or shunts) fall within this denomination, since with all these vessels the problem of closing the wound after medical intervention occurs.

In many invasive interventions in human and animal bodies the physician needs to gain access to an artery or an arterial vessel. Such invasive interventions are for example catheter examinations of any kind, like arteriographies at the heart, in the brain and so on by means of X-ray (roentgen) contrast medium injected into an artery; balloon dilatations or millings of arteries; thrombectomies; functional examinations of the left heart or bringing drugs to defined blood irrigated areas, like for example to the coronary arteries for lysis.

Patients undergoing chronic hemodialysis are equally concerned, since, in order to clean the blood outside the body, an easily accessible arterialized vessel has been operatively provided. For example, this vessel can be a vein of the patient itself or an inserted plastic tube short circuited with the artery (shunt).

After each blood cleansing procedure, that means several times a week the same problem occurs, since the aspirated shunt is difficult to close.

The blood is pressed with a pressure of 133,322–266,644 mbar through the puncture of the vascular wall into the open air or into the tissue surrounding the artery. Due to the relatively high pressure in the artery, a lot of blood gets lost in a very short period of time and undesirable hematomae can arise in the surrounding tissues.

Loss of blood and hematomae are absolutely to be avoided. Up to now this has been achieved by exerting an adequate pressure onto the artery or the arterial vessel with the finger.

This pressure can be adjusted individually according to the blood pressure in the vessel and to the depth and consistency of the covering tissue. It varies interindividually (from one patient to another) and intraindividually (depending on changes in the blood pressure, especially on dropping of the blood pressure of one specific patient) and has to be continuously controlled and adjusted.

If the pressure exerted is to weak, a hematomae of considerable dimensions having several liters can occur, may cause serious consequences. A few consequences which have to be avoided are quoted below by way of example: hemodynamic difficulties, i.e. blood circulation problems occuring when the remaining, intravascular blood volume cannot compensate the blood loss any more; compartment syndromes, i.e. compression of important structures (nerves, shunt) by the hematoma (or by the pressure of an additionally developing edema), the compression destroying these structures; local sterile inflammatory responses during resorption and organization (tissue reconstruction) of the hematoma; infection of the hematoma; and possibly the necessity to remove operatively the hematoma with further risks like infection, abscess, secondary wound healing, and so on.

On the other hand, the exerted pressure should not be too strong, since in that case, the blood vessel would completely collapse. Possible consequences of a too strong pressure are disturbances of the blood supply in subsequent structures (e.g. in a leg and so on) with its possible irreversible loss due to the ischemic tissue damage or, particularly with dialysis patients, shunt occlusion due to thrombogenesis following hemostasis.

2. Description of Related Art including information Disclosed Under 37 CFR § 1.97–1.99

Due to the serious complications involved, inaccurate systems of puncture closure like clamps or circular tourniquets and so on could not find acceptance. The same applies to the puncture closures proposed in the EP 0 554 602 and EP 0 514 026. These puncture closures have a pressure chamber fastened onto the body by means of a surrounding tape and inflated with air pressure. The expansion of the pressure chamber generates a pressure onto the tissue surrounding the puncture closure. Herewith the manually exerted pressure is simply replaced by a pressure bandage, whereas the above mentioned problems of an accurate adjustment to the momentaneous situation still remain.

That is why the pressure is still exerted with the finger, since, thanks to the tactile sense, pressure can be individually varied and adjusted.

But often the patient is not able to exert this pressure with his finger. A debilitation within the frame of the basic disease, a sedation because of the completed examination or the lack of experience are making it impossible for the patient to execute by himself the above mentioned activity.

This means that the nursing or the medical staff has to take on the job of doing it, so that a considerable period of time, namely between 10 and 60 minutes, is blocked for this activity.

This requires a lot of time from the nursing and the medical staff and for the bearer it is expensive and inefficient. Moreover, the above mentioned complications prove that the best solution used up to now is not yet good enough.

SUMMARY OF THE INVENTION

Taking this into consideration, the object of the present invention is to create a puncture closure able to close the puncture of a blood vessel reliably, without a great loss of blood, without generating hematomae or without the complete collapse of the blood vessel.

The invention is based on the finding that the blood will flow out of the arterial vessel until an adequate counter pressure has built up in the surrounding tissue, that is a pressure corresponding to the blood pressure. In case the puncture of the arterial vessel is not constricted manually, the blood flows into the surrounding tissue and there creates the increase of pressure needed to stop bleeding. By receiving the additional (blood) volume, the tissue swells locally and presses onto the puncture. As soon as the pressure exerted by the tissue corresponds to the blood pressure, a pressure balance is achieved at the puncture of the arterial vessel, stopping the bleeding.

One solution of the above mentioned object is that the opening for receiving the pressure medium is located above a puncture channel of the puncture and that the blood flowing out of the blood vessel itself serves as pressure medium.

During an invasive intervention in which an artery is opened, a so called puncture channel is created. This puncture channel leads from the puncture orifice of the blood vessel directly via the covering tissue into the skin and is obvious on the body's surface. For example, if something is injected into the artery with a syringe, the puncture done by the cannula constitutes the puncture channel. Once the cannula is removed, the blood flows through the puncture of the artery into this puncture channel and then outside the body. Now, if the blood streaming out is collected in the pressure chamber of the puncture closure according to the invention, several advantages can be obtained:

1. The blood is collected in a controlled way, leading to an increased hygiene at the patients bed;
2. This blood is used as pressure medium with the result, that within a very short period of time, the arterial pressure builds up in the pressure chamber of the puncture closure and presses onto the tissue surrounding the puncture channel and the pressure in the tissue increases simultaneously;
3. The blood is reliably prevented from flowing into the tissue and the formation of hematomae is excluded;
4. A pressure adjustment in the puncture closure is individually adapted to the person and the situation with the result, that the blood stops flowing out of the artery in the very minute when the pressure in the pressure chamber is the same than the one in the artery. Since the pressure chamber has only a very small capacity, the desired pressure is reached very soon;
5. The patient does not suffer a considerable blood loss.

Once hemostasis and blood coagulation occurred, the puncture closure can be removed without any difficulty.

In a particularly preferred embodiment of the puncture closure according to the invention the pressure chamber comprises an extensible receptacle that is closed except for the opening for receiving the pressure medium.

The advantage of this embodiment is that, once filled with the pressure medium, the pressure chamber can extend freely and exert the desired pressure onto the body part, particularly onto the tissue lying underneath the skin.

In another embodiment, the receptacle is fastened, preferably adhered, onto the retaining tape. The part of the extensible receptacle fastened on the retaining tape constitutes thus, together with the retaining tape itself, a nearly rigid retaining wall and the remaining part of the receptacle constitutes an extensible pressure wall.

The advantage of this embodiment is that its fabrication becomes inexpensive, since the pieces used are all simple and even without any undercut.

In another, preferred embodiment of the puncture closure according to the present invention, the body facing part of the pressure chamber is designed as an extensible pressure wall and the part of the pressure chamber being away from the body is designed as a nearly rigid retaining wall.

In another, particularly preferred embodiment of the puncture closure according to the invention, the extensible pressure wall is fastened onto a carrier element fastened, preferrably adhered, onto the retaining tape, so as to be pressure sealed.

In a particular embodiment, the nearly rigid retaining wall is formed by the retaining tape and the extensible pressure wall is pressure sealed and fastened, preferrably adhered onto the retaining tape.

The advantage of this embodiment is that the puncture closure is inexpensive and can be manufactured with low material costs.

The advantage of the last mentioned embodiments is that the nearly rigid retaining wall prevents the pressure chamber to extend away from the body, so that the given pressure exclusively extends the pressure wall. But since the pressure wall is near the body, the given pressure can be completely used for exerting pressure onto the tissue. Thus, the desired effect can already be achieved with a small volume.

In another embodiment, the retaining tape is a fabric tape, a plaster, a plastic tape, an incision foil or similar. The puncture closure can be manufactured at low costs, using a retaining tape of this kind.

In another, preferred embodiment of the puncture closure according to the invention, the retaining tape is breathable.

The advantage of this embodiment is that underneath the tape the skin still can breathe.

In another embodiment, the retaining tape is provided at least partially with adhesive on the body facing side. Thus, the retaining tape and with it the puncture closure can be adhered onto the desired body part in a fast and easy way.

In a preferred embodiment, the extensible pressure wall or the extensible receptacle are made of rubber, latex, silicone or synthetic material or the like.

The advantage of this embodiment is that the pressure chamber can be extended with little strength and that the given pressure can be completely used for exerting pressure onto the tissue.

In another, preferred embodiment the pressure chamber is filled with hemostatic agents (hemostatica), disinfectants or the like. This accelerates the blood coagulation.

In another embodiment according to the invention the pressure chamber is provided with a filling agent that swells as soon as it gets in touch with the pressure medium. Gauze, cotton or a swelling plastic material are used as filling agent.

The advantage of this embodiment is that the pressure needed in the pressure chamber to close the wound is reached much faster and that the blood loss of the patient can further be reduced.

In another embodiment, the opening in the retaining wall can be closed with a stick on closing element. Thus, the opening made by the cannula in the retaining wall can be closed in a reliable and pressure sealed way.

In further embodiments, a filling agent or a pressure pad are provided at the closing element.

The advantage of both is that the pressure needed in the pressure chamber is achieved much faster and that the patient looses far less blood.

Further advantages of the device according to the invention will become clear in the description of the different embodiments and of the drawing enclosed. The characteristics mentioned above and those mentioned below can be carried out according to the invention either individually or in any combination. The embodiments mentioned are only examples and are not limiting the scope of the invention. Embodiments of the invention are shown in FIGS. 1 to 6 of the drawing and will be described more in detail in the following.

DESCRIPTION OF THE PREFERRED EMBODIMENT

Figure 1:
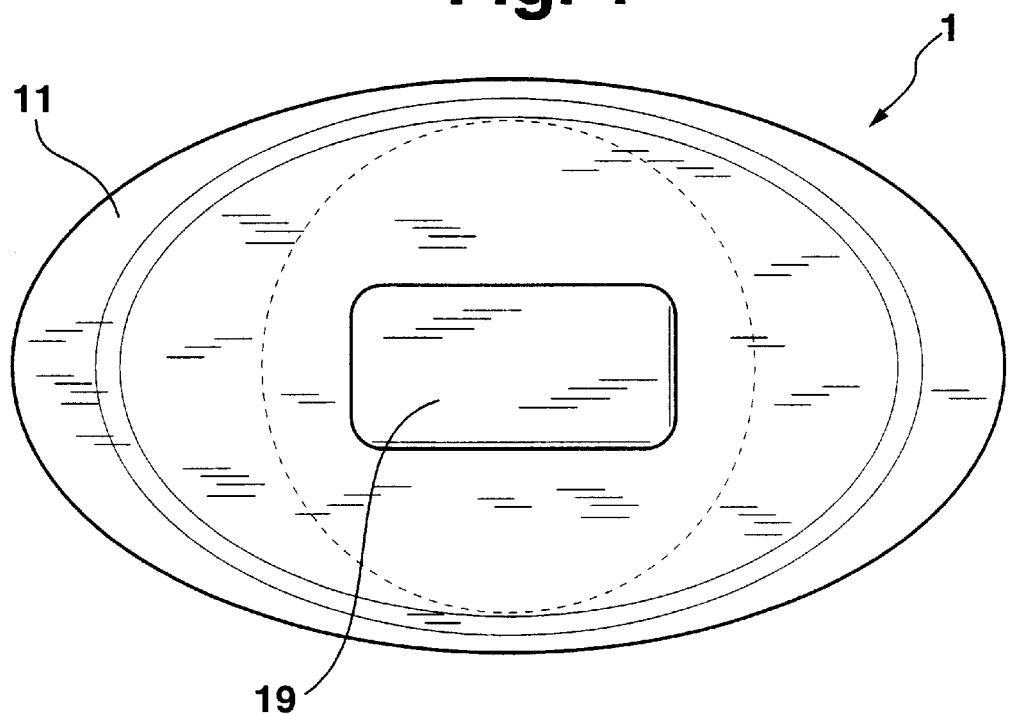
FIG. 1 is a top view of a first embodiment of a puncture closure according to the present invention.

The different figures of the drawing show the object according to the invention in parts in a very simplified way and are not true to scale. The objects of the different figures are in parts superproportionally enlarged so that their structure becomes more obvious.

Figure 2:
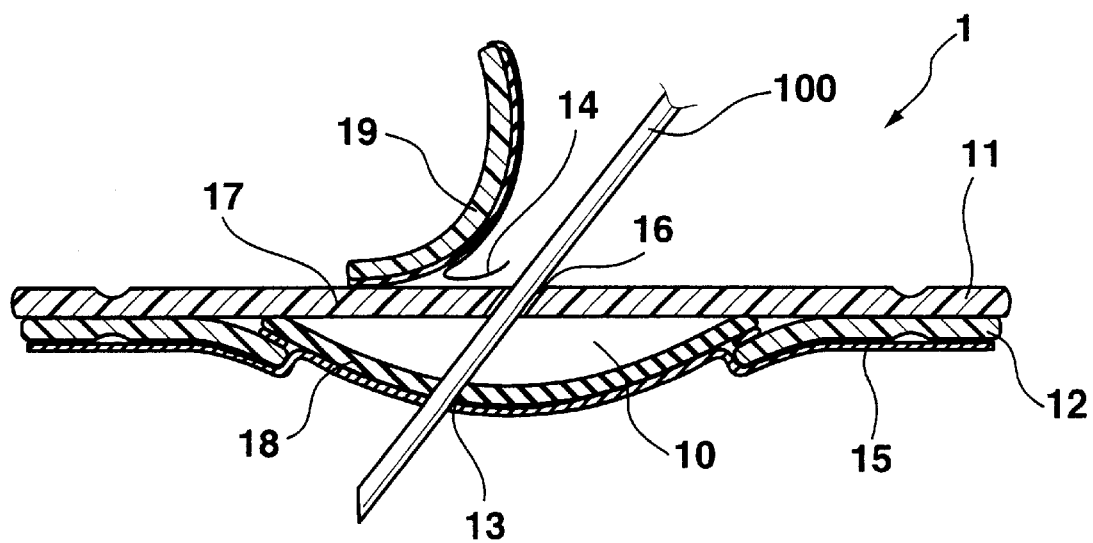
FIG. 2 is a lateral section of the puncture closure according to FIG. 1.

The FIGS. 1 and 2 show a first embodiment of a puncture closure according to the invention, whereas the puncture closure 1 shown has an essentially oval shape. In other embodiments the puncture closures can also have a round, triangular, square or any other shape.

The puncture closure 1 comprises an almost inextensible retaining tape 11, a carrier element 12, an extensible pressure wall 18 and a closing element 19. The carrier element 12 has a circular opening into which the extensible pressure wall 18 is inserted. The carrier element 12 and the pressure wall 18 are adhered together in the area where they are overlapping, so that a pressure sealed connection is achieved, whereas the pressure wall 18 is located between the carrier element 12 and the retaining tape 11. Simultaneously, the retaining tape 11 constitutes a retaining wall 17 of the pressure chamber 10.

The carrier element 12 and the retaining tape 11 are connected together in a pressure sealed way either by bonding and/or by gluing. In this embodiment the carrier element 12 and the retaining tape 11 are made out of the same, little extensible material.

A cannula 100 used to carry out the invasive intervention is inserted into an opening 13 of the extensible pressure wall 18 and into an orifice 16 of the almost inextensible retaining wall 17. Once the invasive intervention is finished and the cannula 100 has been removed, the orifice 16 can be closed by means of a closing element 19. Thereby, the closing element 19 is adhered onto the retaining tape 11. A protection foil 14 covers the tacky surface of the closing element 19 and has to be removed before adhering the closing element 19.

The complete bottom part of the puncture closure 1, i.e. its body facing part, is provided with an adhesive being kind to the skin 15, so that the puncture closure 1 can be reliably fastened onto the body.

Figure 3:
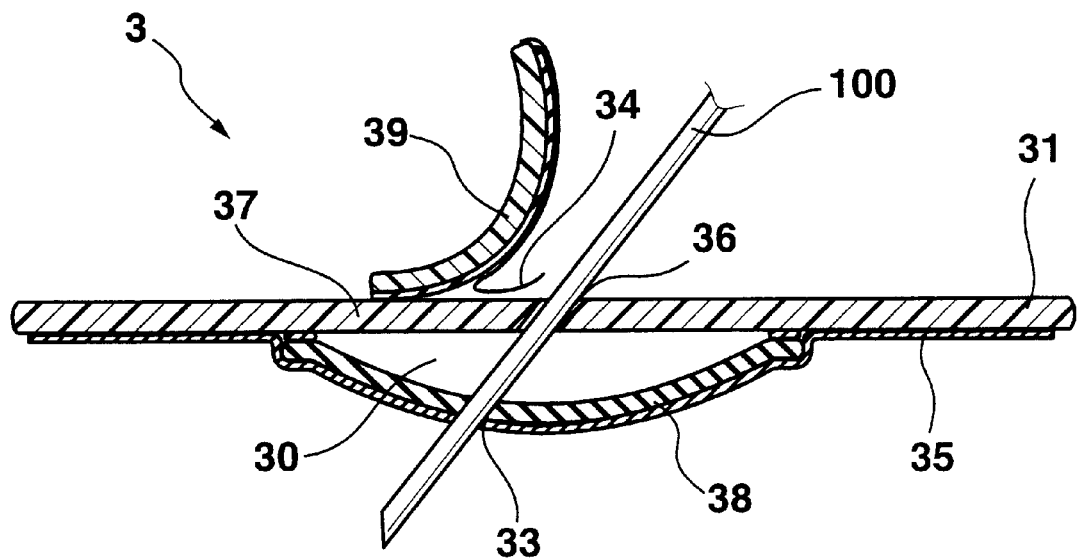
FIG. 3 is a lateral section of a second embodiment of the puncture closure according to the present invention.

FIG. 3 shows a second embodiment 3 of a puncture closure according to the present invention, in which an extensible pressure wall 38 is adhered onto a retaining tape 31 in order to form a pressure chamber 30. Thereby, the retaining tape 31 constitutes simultaneously a retaining wall 37 of the pressure chamber 30. A cannula 100 used to carry out the invasive intervention is inserted into an opening 33 of the extensible pressure wall 38 and into an orifice 36 of the almost inextensible retaining wall 37. Once the invasive intervention is done and the cannula 100 has been removed, the orifice 36 can be closed by means of a closing element 39. Thereby too, the closing element 39 is adhered onto the retaining tape 31. A protection foil 34 covers the tacky surface of the closing element 39 and has to be removed before gluing the closing element 39.

Here too the body facing part of the puncture closure 3 is provided with an adhesive 35.

Figure 4:
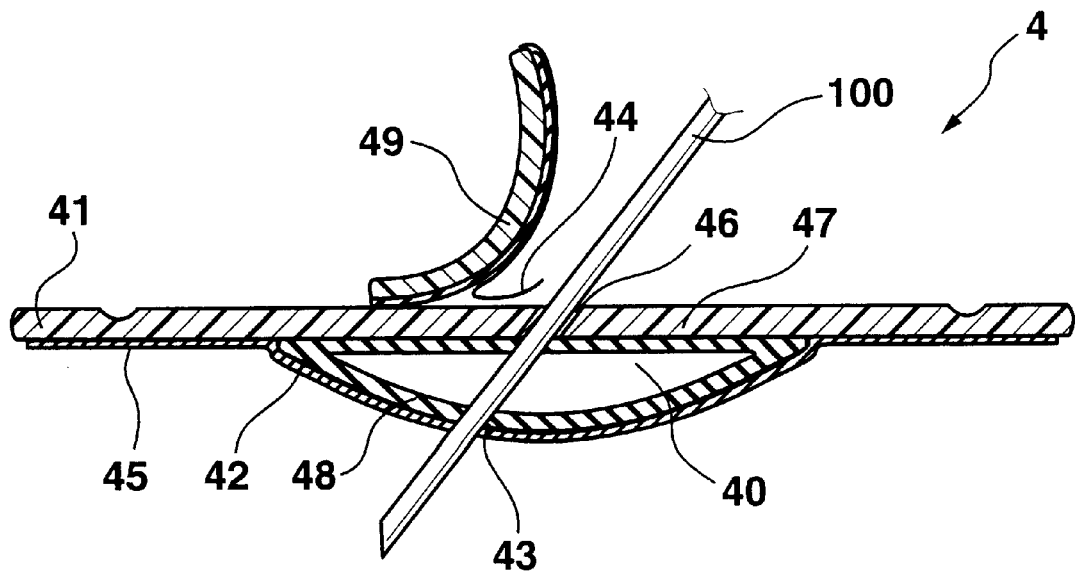
FIG. 4 is a lateral section of a third embodiment of the puncture closure according to the present invention.

FIG. 4 shows a third embodiment 4 of an puncture closure according to the present invention having a pressure chamber 40 comprising an essentially closed receptacle 42. Hereby, the receptacle 42 is adhered onto a retaining tape 41, so that the part of the receptacle 42, which is fastened onto the retaining tape 41 constitutes a retaining wall 47. The remaining part of the extensible receptacle 42 constitutes an extensible pressure wall 48. Here also, a cannula 100 is inserted into an orifice 46 of the retaining wall 47 and into an opening 43 of the pressure wall 48. The orifice 46 is also closed with a closing element 49 provided with a protection foil 44.

The body facing part of the puncture closure 4 is also provided with an adhesive 45.

Figure 5:
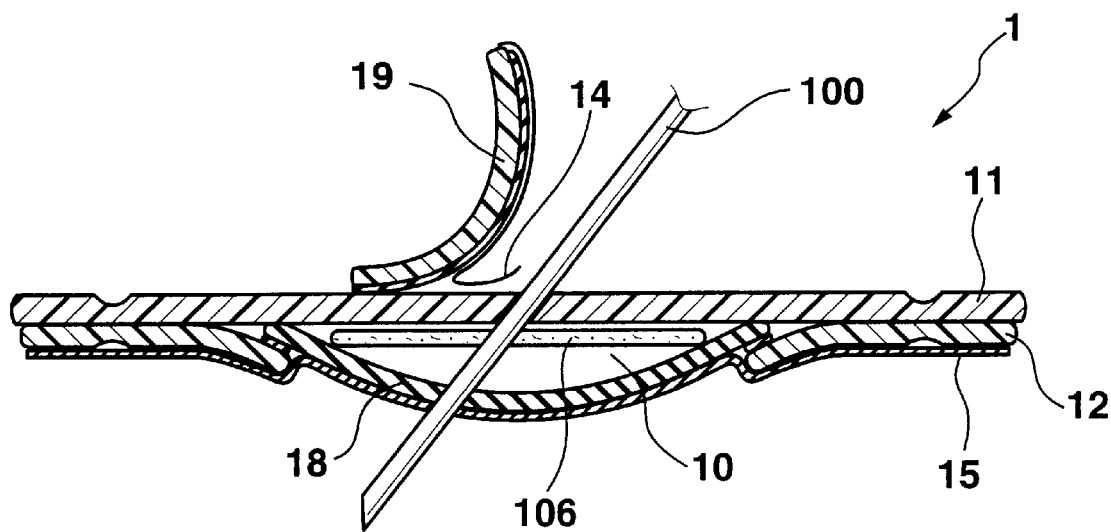
FIG. 5 is a lateral section of the puncture closure according to FIGS. 1 and 2, whereas the pressure chamber is filled with a filling agent.
Figure 6:
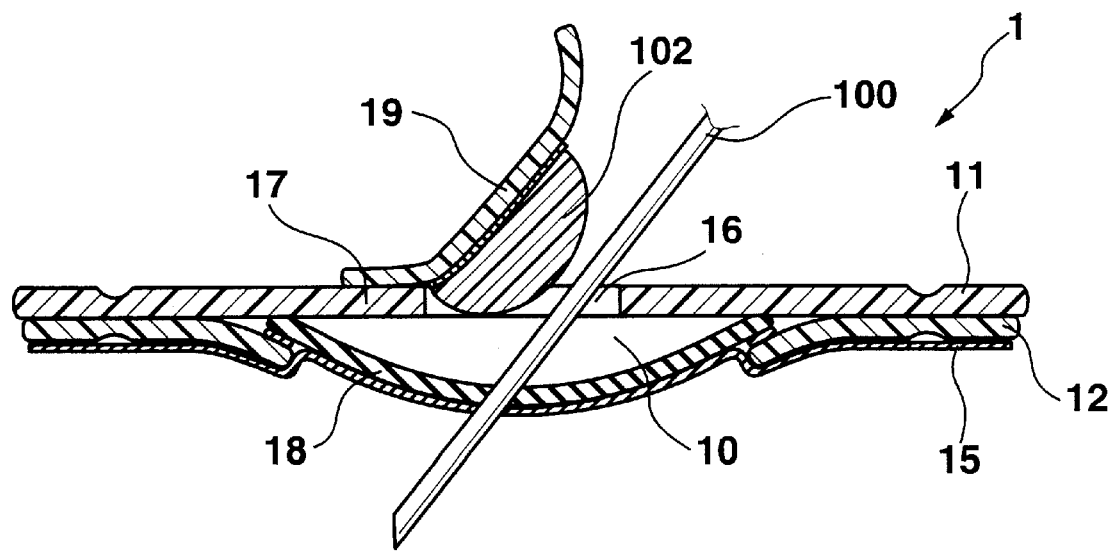
FIG. 6 is a lateral section of the puncture closure according to FIGS. 1 and 2, whereas an additional pressure pad is provided.

The FIGS. 5 and 6 show further developments of the first embodiments. These developments can also be applied to other embodiments without leaving the scope of the invention.

The pressure chamber 10 of the puncture closure 1 shown in FIG. 5 contains a filling agent 106 that is used to fill the space in the pressure chamber 10 in advance, so that less blood is needed to reach the desired pressure. This effect is increased when the filling agent 106 used is a material which swells as soon as it gets in touch with blood. Gauze, cotton, swelling synthetic material or the like are preferably used as filling agent 106.

The puncture closure shown in FIG. 6 has a very big orifice 16, into which a pressure pad 102 fastened onto the closing element 19 is engaged. The pressure pad 102 is made hereby of a nearly incompressible material.

The pressure pad 102 is needed to create in the pressure chamber 10 a certain basal volume. This basal volume gets complemented by the blood flowing into the pressure chamber 10 and speeds up the filling procedure of the pressure chamber 10, so that the desired pressure is reached much earlier. This reduces considerably the needed blood quantity, speeds up the hemostasis and reduces the blood loss of the patient.

Such a pressure pad 102 can also be used in an puncture closure according to the FIGS. 3 or 4.

The pressure chamber 10, 30, 40 of the puncture closures according to the FIGS. 1 to 4 can alternatively or additionally to the pressure pad 102 be provided with a filling agent 106.

In the above mentioned puncture closures 1, 3, 4 the retaining tape 11, 31, 41 as well as the carrier element 12 is made of an almost rigid material, i.e. of a material that does not extend considerably under pressure or traction. The retaining tapes 11, 31, 41 and the carrier element 12 can for example be made of a tissue tape, a plaster, a not yielding synthetic tape or the like. In the embodiments shown, the retaining tapes 11 and the carrier element 12 is made of incision foil.

The pressure walls 18, 38, 48 and the extensible receptacle 42 of the above mentioned puncture closures 1, 3, 4 are made of a very extensible and/or elastic material that can be extended or enlarged without using a lot of strength. This material can be rubber, latex, extensible plastic or the like.

Before undertaking an invasive intervention, the physician takes one of the above mentioned puncture closures 1, 3, 4 and adheres it onto the body part where the invasive intervention has to occur. He then inserts the cannula 100 with its syringe into the artery. He thus achieves that the insertion channel created by the cannula 100 is in alignment with the opening 13, 33, 43.

Once the invasive intervention is over, the physician removes the syringe and its cannula 100 from the artery and out of the puncture closure 1, 3, 4 and closes the orifice 16, 36, 46 in the retaining wall 17, 37, 47 of the puncture closure 1, 3, 4 by gluing the prepared closing element 19, 39, 49 onto the orifice 16, 36, 46. This adhesive should be pressure sealed enough, so that the blood flowing out of the artery through the insertion channel into the pressure chamber 10, 30, 40 can build up the pressure necessary to close the wound without the pressure chamber 10, 30, 40 becoming leaky.

Now, the arterial blood flows directly into the pressure chamber 10, 30, 40 of the puncture closure 1, 3, 4 and not into the surrounding tissue, since the flow resistance against the blood is higher in the tissue than in the puncture closure 1, 3, 4. As soon as the pressure chamber 10, 30, 40 is filled, an excess pressure builds up under which the pressure chamber 10, 30, 40 expands by its extensible pressure wall 18, 38, 48.

An extension of the almost rigid retaining wall 17, 37, 47 is not possible, since the retaining wall 17, 37, 47 is not extensible and does not yield.

The expanding pressure wall 18, 38, 48 presses onto the tissue in the vicinity of the insertion channel and increases thus the pressure onto the tissue. The pressure in the pressure chamber 10, 30, 40 and the one in the tissue are thus build up nearly simultaneously, so that the blood will always flow into the pressure chamber 10, 30, 40 and not into the tissue. As soon as the pressure in the pressure chamber 10, 30, 40 corresponds to the blood pressure, balance is achieved between the artery and the pressure chamber 10, 30, 40, and no more blood flows into the pressure chamber 10, 30, 40. Now bleeding has stopped and the blood can coagulate. Coagulation can be speeded up by giving additives into the pressure chamber like e.g. hemostaticae or the like.

Once the wound is closed, the puncture closure 1, 3, 4 can be removed from the body and can be correctly disposed of.

| List of reference numbers | | | |
|---|---|---|---|
| 1 | 3 | 4 | puncture closure |
| 10 | 30 | 40 | pressure chamber |
| 11 | 31 | 41 | retaining tape |
|  |  | 42 | receptacle |
| 12 |  |  | carrier element |
| 13 | 33 | 43 | opening |
| 14 | 34 | 44 | protection foil |
| 15 | 35 | 45 | adhesive |
| 16 | 36 | 46 | orifice |
| 17 | 37 | 47 | retaining wall |
| 18 | 38 | 48 | pressure wall |
| 19 | 39 | 49 | closing element |
|  |  | 100 | cannula |
|  |  | 102 | pressure pad |
|  |  | 106 | filling agent |

We claim:

1. Puncture closure to close a puncture of a blood vessel in body tissue of a patient which is under arterial pressure, the puncture including a puncture channel, said puncture closure comprising an outer layer of material and an inner layer structure with a pressure chamber (10, 30, 40) formed between said outer layer and said layer structure, which chamber is loadable with arterial pressure, said layer structure having an opening (13, 33, 43) for receiving a pressure medium which is the arterial blood pressure of a patient, said layer structure being capable of being fastened onto the body tissue of the patient in the vicinity of the puncture, the body tissue facing part of said pressure chamber (10, 30, 40) being extensible, said opening (13, 33, 43) for receiving the pressure medium being arranged within the body tissue for communicating with said pressure chamber (10, 30, 40), so that said opening (13, 33, 43) can be located above the puncture channel of the puncture and so that the blood flowing out of the puncture of the blood vessel itself can flow into said pressure chamber (10, 30, 40) for acting as the pressure medium.

2. Puncture closure according to claim 1, wherein the body tissue facing said pressure chamber (10, 30, 40) is designed as an extensible pressure wall (18, 38, 48) and said outer layer defining a side of said pressure chamber (10, 30, 40) and located away from the body being a non-extensible retaining wall (17, 37, 47).

3. Puncture closure according to claim 2, being constructed and arranged to receive a cannula (100) which is inserted through said retaining wall (17, 37, 47) and through opening (13, 33, 43) for receiving some arterial blood.

4. Puncture closure according to claim 3, wherein said retaining wall has an opening through which a cannula can be inserted.

5. Puncture closure according to claim 4, wherein said opening is closed by a closing element (19, 39, 49) which is adhered onto said retaining wall (17, 37, 47).

6. Puncture closure according to claim 5, wherein one of a filling agent (106) or a pressure pad (102) is connected to said closing element (19).

7. Puncture closure according to claim 2, wherein said non-extensible retaining wall (37) is made of a retaining tape (31) and wherein said layer structure includes an extensible pressure wall (18 or 38) which is fastened or adhered in a pressure sealed way onto said retaining tape.

8. Puncture closure according to claim 7, wherein said extensible pressure wall (18 or 38) is made of rubber, latex, synthetic material or the like.

9. Puncture closure according to claim 3, wherein said retaining tape (11, 31, 41) is is made of a porous material.

10. Puncture closure according to claim 7, wherein extensible pressure wall (18 or 38) is fastened or adhered in a pressure sealed way onto a carrier element (12) fastened onto said retaining tape (11).

11. Puncture closure according to claim 10 wherein said retaining tape (11, 31, 41) is at least partially provided with an adhesive (15, 35, 45) on a side thereof facing body tissue.

12. Puncture closure according to claim 1 wherein said pressure chamber (40) is defined within an extensible walled receptacle (42), said receptacle (42) being closed except for said opening (43) for receiving the pressure medium.

13. Puncture closure according to claim 12, wherein a wall of said extensible receptacle (42) is fastened or adhered onto said retaining tape (41).

14. Puncture closure according to claim 12, wherein said extensible walled receptacle (42) is made of rubber, latex, or synthetic material.

15. Puncture closure according to claim 1, wherein said pressure chamber has a coagulation agent, a disinfectant, or a hemostatica therein.

16. Puncture closure according to claim 1, wherein said pressure chamber has a filling agent (106) therein.

17. Puncture closure according to claim 16, wherein said filling agent (106) is made of a material, which swells when blood comes in contact with said filling agent.

18. Puncture closure according to claim 17, wherein said filling agent (106) is made of gauze, cotton, or swelling synthetic material.

* * * * *